United States Patent [19]

Zimmerman

[11] Patent Number: 4,894,225

[45] Date of Patent: Jan. 16, 1990

[54] COMBINATION THERAPY USING ANTITUMOR IMMUNOTOXINS WITH TUMOR NECROSIS FACTOR

[75] Inventor: Robert Zimmerman, Lafayette, Calif.

[73] Assignee: Cetus Corporation, Emeryville, Calif.

[21] Appl. No.: 20,443

[22] Filed: Mar. 2, 1987

[51] Int. Cl.[4] .................... A61K 37/02; A61K 39/00; A61K 39/395

[52] U.S. Cl. .................... 424/85.1; 424/85.9; 514/2; 514/8; 514/21; 514/885; 530/351; 530/391

[58] Field of Search .................... 424/85, 85.1, 85.91; 514/2, 8, 21, 885; 530/351, 391

[56] References Cited

U.S. PATENT DOCUMENTS 4,650,674  3/1987  Aggarwal et al. .................... 514/2

FOREIGN PATENT DOCUMENTS 0131789  1/1985  European Pat. Off. .
0168214  1/1986  European Pat. Off. .

OTHER PUBLICATIONS

Winkelhake et al., CA vol. 107 (11) #95043f.
Hadden, "The Case for Synergistic Combinations in Immunotherapy", 14th International Cancer Congress 8/21-27/86.
Dr. Talmadge, Preclinical Screening Lab, BRMP (1986).

*Primary Examiner*—Garnette D. Draper
*Attorney, Agent, or Firm*—Gregory J. Giotta; Janet E. Hasak; Albert P. Halluin

[57] ABSTRACT

Tumor necrosis factor and a suitable immuotoxin when administered simultaneously or in tandem produce a synergistic effect in treating tumor burden in warm-blooded animals. Methods and protocols for obtaining this syneristic effect are disclosed, as well as compositions effective in this treatment.

9 Claims, No Drawings

COMBINATION THERAPY USING ANTITUMOR IMMUNOTOXINS WITH TUMOR NECROSIS FACTOR

FIELD OF THE INVENTION

The invention relates to use of a combination of tumor necrosis factor (TNF) and a suitable immunotoxin in the treatment of cancer in mammals. In particular, it relates to therapeutic or prophylactic antitumor treatment in mammals using simultaneous or alternate administration of these components.

BACKGROUND ART

Both immunotoxins and TNF have been demonstrated to produce antitumor activity in mammals. As with any treatment using potent chemotherapeutic agents, toxic side effects may occur. These effects may be minimized if the dosage levels are kept as low as possible. By utilizing a combination of TNF and a suitable immunotoxin the dose level of each component can be reduced, thus preventing the toxicity which might otherwise be encountered at the ordinarily used dosaqe levels.

TNF itself is, of course, noted for its ability to hamper tumor growth and kill tumor cells. An extensive literature on TNF per se exists, and the gene encoding native TNF proteins has been cloned and expressed.

Tumor necrosis factor (TNF) was first described by Carswell et al, *Proc Natl Acad Sci USA* (1975), 72:3666–3670. as an endotoxin-induced serum factor which causes necrosis of chemically transformed tumor cells when growing in mice. Purified preparations of murine TNF have been tested against murine and human cell lines in vitro: Haranaka, K., and Satomi, N., *Japan J Exp Med* (1981) 51:191. In contrast to normal cells, tumor cell lines from both species were susceptible to the cytotoxic activity of the mouse TNF. Furthermore, the murine TNF was reported to be toxic against both human and mouse-transplanted tumors in nude mice. See Haranaka, K., et al, *Int J Cancer* (1984) 34:263–267. Human TNF is also known to be cytotoxic to neoplastic cells, and has been produced in recombinant form. See Pennica et al. *Nature* (1984) 312:724–729; Shirai et al, *Nature* (1985) 313:803–806; Wanq et al, *Science* (1985) 228:149–154.

The cloning of rabbit TNF is disclosed in EP No. 146,026. published 26 June 1985 (Dainippon Pharmaceutical Co., Ltd.) and EP No. 148,311, published 17 July 1985 (Asahi Kasei Kogyo Kabushiki). The cloning of human TNF having 151 and 155 amino acids (2 and 6 less than the human native form) is disclosed in EP No. 155,549, published 25 Sept. 1985 (Dainippon Pharmaceutical Co., Ltd.), and human TNF having 155 amino acids is disclosed in EP No. 158,286, published 16 Oct. 1985 (Asahi Kasei Koqyo Kabushiki Kaisha) corresponding to GB No. 2,158,829A, published 20 Nov. 1985. The cloning of mature TNF (157 amino acids) and various modified forms (muteins) thereof is disclosed in EP No. 168,214, published 15 Jan. 1986 (Genentech) and PCT U.S. Pat. No. 85/01921, filed 3 Oct. 1985. published Apr. 1986 (Cetus Corporation). The latter, PCT No. 85/01921, corresponds to U.S. Ser. No. 760,661 filed 30 July 1985, now U.S. Pat. No. 4,677,063 the disclosure of which is incorporated herein by reference.

The literature on potential immunotoxins against tumors is also extensive. In most constructions, the tumor specificity is provided by an antibody or fragment thereof which is immunoreactive with tumor surface antigens. Both polyclonal sera raised against tumor antigens and monoclonal antibody preparations have been employed. The remainder of the immunotoxin is a cytotoxic moiety which can be chosen from a broad range of candidates.

Antisera and monoclonal preparations against a variety of tumors have been prepared and are known in the art. In particular, murine monoclonal antibodies that bind selectively to human breast cancer cells have been prepared. When conjugated to ricin A chain to form an immunotoxin, these antibodies exhibit a tissue culture inhibitory dose which results in 50% of control (untreated) protein synthesis (TCID 50%) of less than about 10 nM against at least one of MCF-7, CAMA-1, SKBR-3. or BT-20 cells. These antibodies are described more fully in EPC Patent Publication No. 153,114, published 28 Aug. 1985, the disclosure of which is incorporated herein by reference.

Similar murine monoclonal antibodies have been used for imaging. These antibodies do not bind to blood cells, and have a breast tumor binding range of at least 0.25 (i.e., they bind to at least 25% of breast tumors tested). These antibodies include most of those described above and are described in copendinq U.S. application Ser. No. 786,948, filed 11 Oct. 1985, assigned to the same assignee and incorporated herein by reference.

Combination chemotherapy in general using two or more anti-cancer drugs to treat malignant tumors in humans is currently in use in research and in the clinic. The anti-cancer druqs may be antimetabolites, alkylating agents, antibiotics, general poisons. etc. Combinations of drugs are administered in an attempt to obtain a synergistic cytotoxic effect on most cancers, e.g., carcinomas. melanomas, lymphomas and sarcomas and to reduce or eliminate emergence of drug-resistant cells and reduce side effects of each drug. Dr. Talmadge of the Preclinical Screening Lab, BRMP reported in 1986 the augmented effect of using TNF and γ-IFN to treat metastatic disease in mice. EP publication No. 131,789 published 23 Jan. 85 (Sloan-Kettering Institute for Cancer Research) and EP No. 168,214 published 15 Jan. 85 (Genentech) disclose the synergistic effect of the TNF and λ-IFN to treat various tumors in mice. However, applicants are unaware of any demonstration of synergistic effects against tumors by combinations of suitable immunotoxins with TNF.

DISCLOSURE OF THE INVENTION

The invention provides a means for lowering the dosage of individual immunotoxins and TNF preparations by alternate or simultaneous administration of combinations thereof. The preparations have a therapeutic and/or prophylactic effect on tumor tissue when administered in combination which is significantly greater than the sum of the effects of each administered alone. Hence, when administered in combination, the dosaqe level of each component may be siqnificantly lowered, thus producing the same result with less toxic, or other undesirable, side effects.

Accordingly, in one aspect the invention is directed to a method of therapeutic or prophylactic treatment of tumors in warm-blooded animal subjects by administering a combination of an appropriate immunotoxin and TNF. In other aspects, the invention is directed to pharmaceutical compositions containing combinations of immunotoxin and TNF. and to specific administration protocols for these two agents.

The method of the invention involves administering to a warm-blooded animal subject, including mouse, rabbit, primate, human, avian, or other warm-blooded species, a pharmacologically effective amount (in combination) of immunotoxin appropriate to the tumor to be treated and TNF. The two active ingredients may be combined in vitro before administration, as long as neither is adversely affected chemically and both remain biologically effective. They may, however, be separately administered to the subject or patient, either in a staggered sequence or simultaneously, but, in any event, as part of the same treatment protocol.

DETAILED DESCRIPTION OF THE INVENTION

A. Definitions

As used herein, "therapeutic" treatment refers to administration of the combination of the invention to a subject after a tumor burden has been determined in that subject using any method known in the art, and with resultant decrease or elimination of the tumor burden.

"Prophylactic" treatment refers to such administration to prevent recurrence of the tumor burden after therapeutic treatment has been administered.

"Tumor burden" refers to any neoplastic disorder including such cellular disorders as, for example, renal cell cancer Kaposi's sarcoma chronic leukemia, breast cancer, sarcoma, ovarian carcinoma, rectal cancer, throat cancer, melanoma, colon cancer, bladder cancer, mastocytoma, lung cancer and gastrointestinal or stomach cancer. In the method of the invention, the target tumor burden is advantageously colon cancer, melanoma, renal cell cancer, lung cancer. adenocarcinoma, breast cancer, or ovarian cancer; most advantageously breast and/or ovarian cancer.

"Pharmacologically effective amount" refers to the total amount of the active ingredients in the methods or preparations of the invention which is sufficient to produce a therapeutic and/or prophylactic effect on the tumor burden. As applied to an individual active ingredient administered alone, of course, the "pharmacologically effective amount" refers to that ingredient alone; however when the combinations of the invention are used, "pharmacologically effective amount" refers to the combined amounts in the preparation which result in the therapeutic or prophylactic effect of the combination.

"Pharmaceutically acceptable excipient" refers to an excipient which does not interfere with the effectiveness of the active ingredients, and which is nontoxic to the subject.

"Selective binding to subject tumor cells" refers to the capacity of the immunotoxins herein to bind preferentially to tumor cells as opposed to normal healthy cells. This selective binding is conferred by the portion of the immunotoxin which is conventionally an antibody or derived from an antibody, such as an immunoreactive fragment. A wide range of antibodies is available in the art which provides antibodies selective for a large number of tumors including the various tumors listed under the definition of tumor burden above. Selection is made among these antibodies or fragments in constructing the immunotoxin suitable for the tumor burden to be treated.

The American Type Culture Collection (ATCC). Rockville, MD USA has a wide variety of cell lines on deposit which produce monoclonal antibodies to target tumors. For example, cell lines producing monoclonal antibodies to human non-small cell lung cancer include 70304 (deposited as ATCC No. HB8301). Cell lines producing monoclonal antibodies to human melanoma cells include 704A1 (deposited as ATCC No. HB8302). Cell lines producing monoclonal antibodies to small cell carcinoma include the cell lines deposited as ATCC HB8462 and ATCC HB8711. Cell lines producing antibodies to pancreatic carcinoma of ductal origin include the hybridoma deposited as ATCC HB8504. A cell line producing antibodies which bind to the epitope present on adenocarcinomas of the stomach, colon, and pancreas, and to esophagus, breast and ovarian tumors, known as CSLEX1, is deposited as ATCC HB8580.

With respect to an exemplified antibody, such as the exemplified monoclonal antihuman breast cancer antibody, the term "functional equivalent" refers to an antibody preparation which is cross-reactive with the exemplified monoclonal antibody in a standard immunoassay procedure. Cross-reactivity is a result of binding to the same epitope or to a region situated sufficiently close to the epitope bound by the exemplified antibody.

"Suitable immunotoxin" refers to a conjugate of an antibody or immunologically reactive fragment of an antibody and a cytotoxic moiety, wherein the antibody or fragment thereof employed binds selectively to the tumor burden cells, and does so under the circumstance wherein it is conjugated to the toxin. Thus a "suitable immunotoxin" binds selectively to the particular type of tumor, without substantial binding to normal cells. The cytotoxic moiety of the immunotoxin includes a toxic drug or an enzymatically active drug, which may be of bacterial or plant origin. Examples of enzymatically active toxins include diphtheria A chain, nonbinding fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and endomycin. Ricin A chain, nonbinding active fragments of diphtheria toxin, abrin A chain, and PAPII are preferred; ricin A chain is most preferred.

The term "staggered" protocol refers to a regimen for administration of the combination wherein there is a time interval of at least 24 hours between the individual administrations of TNF and immunotoxin in at least one set of such administrations. In "simultaneous" protocols, each separate TNF administration is within 24 hours of each immunotoxin administration. Of course, protocols which employ mixtures of these drugs are "simultaneous".

B. General Description

The immunotoxins and TNF described herein could be used independently: however, according to the invention, advantage is taken of the demonstration that the effect of either TNF or suitable immunotoxin is synergistically enhanced by the presence of the other. Thus, the antitumor activity of each can be markedly increased by the use of the two factors in the same protocol in effecting treatment. Therefore, formulations containing both of them are particularly useful in the practice of the method of the invention. The dosage levels for the combined therapy are, of course, lower than those desired if either were to be administered alone.

The combinations or the individual components for the practice of the invention may be formulated in conventional ways standard in the art for the administration of protein substances. See, for example, *Remington's Pharmaceutical Sciences*, Mack Publishinq Co.. Easton. PA, latest edition. Administration by injection is preferred; formulations include solutions or suspensions, emulsions, or solid composition for reconstitution into injectables. Suitable excipients include, for example, Ringer's solution, Hank's solution, water, saline, glycerol, dextrose solutions, and the like.

The method of the invention involves administering to a warm-blooded animal host, includinq mouse, rabbit, primate, avian, or other warm blooded species a pharmacologically effective amount (in combination) of TNF and immunotoxin appropriate to the tumor to be treated. The two active ingredients may be combined in vitro before administration, as long as neither is adversely affected chemically and both remain effective. They may, however, be separately administered to the patient, either in staggered fashion or simultaneously, but in any event, as part of the same treatment protocol. For example, the immunotoxin and TNF may be administered on alternate days or together every 2-3 days.

Administration may take place by any suitable technique including parenteral administration, such as intravenous, interarterial, intramuscular, subcutaneous or combinations of the above. The subject may be treated locally for a particular tumor, for example, or systemically. The dose and dosage regimen depends on the nature of the tumor, the particular formulation decided upon, and the mode of administration. Administration is in an amount which is nontoxic to the host; toxicity may be monitored by the extent and type of various side effects such as fever, chills and general malaise.

In typical protocols, the TNF and immunotoxin are given in repeated doses, usually over a period of a number of days or weeks. One typical regimen might comprise administering both the TNF and immunotoxin composition on the first day (day 0) followed by additional similar administrations of both compositions on days 3 and 6. Alternatively, for example, the TNF composition miqht be administered on days 0, 2, 4, and 6 while the suitable immunotoxin is administered on day 1, 3, 5 and 7. Suitable dosaqe ranges for these repeated protocols are in the range of 0.1 μg/kg-3mg/kg per dose for TNF and in the range of 10 μg/kg to 3 mg/kg per dose of the suitable immunotoxin. These dosage ranges are, of course, only approximate since for both components the nature of the host and of the tumor burden is of considerable significance: in addition for the suitable immunotoxin, the dosaqe will depend on the nature of the component selectively binding to the tumor and the nature of the toxin. In general, the more selective the bindinq component for the tumor burden cell type, the less immunotoxin is required; also, the more toxic the cytotoxic moiety the less is required.

C. Preparation of the Active Ingredients

The TNF and its muteins useful as active ingredients in the compositions of the invention are prepared either by direct isolation from the cells producing them, or by recombinant techniques, as set forth in the Background Section herein.

Described in the publications set forth in the Background section, and particularly advantageous, is the use of TNF in recombinant forms. TNF protein can be produced conveniently in both procaryotic and eucaryotic expression systems. The complete amino acid sequence for "mature" human TNF containing 157 amino acids and a description of its recombinant production is given by Wang. A., et al. *Science* (1985) 228:149-153. This recombinantly produced mature human TNF is particularly preferred as the TNF component of the invention combination when the subject to be treated is human. Also favored are particular mutein forms of this mature TNF, namely those which are lacking four or eight amino acids from the N-terminus. The preferred TNF for animal subjects other than human typically corresponds to TNF derived from the appropriate species.

Preparation of the immunotoxins is also well known in the art. The antibody component of the conjuqate will be selected according to the nature of the tumor to be treated, and the toxin chosen with particular attention to that effective in the context of the nature of the subject and the particular tumor burden considered. In any event, the antibody portion may be whole antibodies, as a polyclonal or monoclonal preparation, or immunologically reactive fragments of an antibody such as the Fab', Fab or F(ab)$_2$ portions; in all cases these materials are chosen so as to exhibit selective binding to the subject tumor. Thus, of course, antibreast antibodies will be chosen if breast tumors are to be treated, antiovarian tumor antibodies if ovarian tumors are the burden of the subject, and so forth. The toxins may be any of a variety of materials as set forth above, and can be conjugated to the desired antibody by means well known in the art. These include use of bifunctional linkers, and of dehydrating agents. Techniques for preparing such immunotoxins are described in EP Publication No. 153,114, published 8 Feb. 1985, the disclosure of which is incorporated herein by reference.

D. Examples

The following examples are intended to illustrate but not limit the invention. The examples involve use of a tumor model system in nude mice using MX-1, a human breast adenoarcinoma-derived tumor cell line to which the monoclonal antibody 260F9 used hereinbelow is capable of binding. This model system is well known in the art. The particular immunotoxin (IMT) utilized is 260F9-it-srRTA. which contains the human antibreast antibody 260F9 conjugated using 2-iminothiolane (it) to recombinantly produced, soluble ricin toxin A (srRTA). The monoclonal antibody 260F9 is described in U.S. Ser. No. 690,750 filed 11 Jan. 1985, now U.S. Pat. No. 4,753,894 assigned to the same assignee and incorporated herein by reference. In addition, this antibody is deposited at the American Type Culture Collection. ATCC Accession No. HB8488. The soluble ricin toxin A is prepared as described in U.S. Ser. No. 837,583 filed 7 Mar. 1986, assigned to the same assignee and incorporated herein by reference. Conjugation using 2-iminothiolane is as described in EP Publication No. 153,114 above.

The TNF employed in these examples was a recombinantly produced mutein lacking the eight N-terminal amino acids of the mature TNF set forth in Wang. A., et al. *Science* (1985) 228:149-153. The cDNA encoding this mutein preceded by an ATG, was expressed in *E. coli* using appropriate expression vectors, and the resulting protein was purified using standard techniques. The purified protein was lyophilized and stored in this form. For use in these examples, the protein was reconstituted in PBS within four days prior to use and stored at 4° C. The TNF contained <6 pg endotoxin per mg protein.

Various protocols using groups of mice which have been injected subcutaneously with the MX-1 tumors and employing intravenous injections of TNF and/or 260F9-it-srRTA were conducted as described below. In all instances, the combination exerted a greater than additive effect in reducing the tumor and prolonging the life of the subject.

EXAMPLE 1

Athymic mice having 7 day subcutaneous MX-1 tumors 5 mice per group) were treated intravenously using the −8 TNF mutein at 25 μg/kg and 125 μg/kg per dose at 3 day intervals for a total of 3 doses (q3dX3) starting at day 0 and with the immunotoxin at 3.5 μg and 7 =g per dose at 2 day intervals for a total of 6 doses (q2dX6), also starting at day 0. Thus, TNF was administered at days 0, 3 and 6 and immunotoxin at days 0, 2, 4, 6, 8, and 10.

TABLE 1

| grp | day 14 ΔBW | day 21 ΔBW | day 14 ΔTW | day 21 ΔTW | deaths | ΔTW(day 14)as % of control |
|---|---|---|---|---|---|---|
| TNF 125 | 1.09 | 1.05 | 13.6 | 45.0 | 2/5 [d1,d8] | 59 |
| +IMT (3.5) | — | — | — | — | 5/5 [d4,d8(3),d9] | — |
| +IMT (7.0) | — | — | — | — | 5/5 [d1(2),d2(2),d4] | — |
| TNF 25 | 1.10 | 1.17 | 19.0 | 40.0 | 0/5 | 79 |
| +IMT (3.5) | 14.4 | 1.28 | 17.2 | 45.7 | 2/5 [d7] | 72 |
| +IMT (7.0) | 0.98 | 1.04 | 2.7 | 3.2 | 2/5 [d7] | 10 |
| IMT (3.5) | 1.06 | 1.21 | 17.0 | 43.0 | 1/5 [d8] | 68 |
| IMT (7.0) | 1.02 | 1.14 | 7.7 | 25.9 | 2/5 [d4] | 31 |
| PBS Control | 1.15 | 1.20 | 23.9 | 47.0 | 0/5 | 100 |

Table 1 shows the results in the terms of change in weight of tumor (ΔTW) at days 14 and 21 for TNF or immunotoxin (shown as IMT in the Table) alone and in combination. Change in body weight (ΔBW) was also recorded as a measure of toxicity. These data are given as the ratio of the final tumor or body weight to corresponding initial values.

As shown in Table 1, the tumors continued to grow in all cases, but the rate of growth was greatly slowed when TNF or immunotoxin was administered. The effect of administration of the combination was more than additive. Thus, for example, at day 21 for no treatment the increase in tumor weight was 47.0; for TNF alone it was 45.0 or 40.0: and for immunotoxin alone it was 43.0 or 25.9. However, when both TNF at 25μg/kg and immunotoxin at 7.0 μg were administered, the increase in growth was only 3.2.

EXAMPLE 2

In an alternative protocol, comparison was made between the effects of administering TNF and immunotoxin simultaneously and in staggered dosage. All administrations were supplied IV.

In the protocol involving simultaneous delivery of the drugs. TNF was supplied at a level of 25 or 50 μg per kg per dose while the immunotoxin was administered at levels of 3.5 or 7.0 μg per dose, which corresponds to a level of 175 or 350 μg/kg. In the protocol involving staggered treatment, the same total dosage was delivered but TNF was supplied at 50 or 100 μg per kg at each dose to attain the same total dose level. Administration of cytoxan was used as a positive control in each case, PBS as a negative control, and as in Example 1, there were 5 mice in each group.

In the simultaneous protocol, each drug was delivered q2dX6—i.e.. every 2 days for 6 dosages while in the staggered treatment TNF was delivered q4dX3 starting at day 0 and immunotoxin and q2dX6 starting at day 1—i.e.. TNF was administered every 4 days for 3 dosages total, while immunotoxin (IMT) was administered 6 times at 2 day intervals.

The results of each of these protocols are given in Tables 2 and 3. The results are tabulated in terms of change in tumor weight; number of deaths is also given and change in body weight is shown as a measure of toxicity. Percent TGI represents the percentage of tumor growth inhibition as compared to the PBS negative controls.

As shown in Table 2, at low TNF dosage levels, the results in percent tumor growth inhibition (% TGI) were slightly more than additive, although at higher TNF dosages only additive results are obtained. This is common in instances of synergistic behavior wherein optimum effects are achieved at lower dosage levels.

TABLE 2

| group | ΔBW | deaths | ΔTW | % TGI |
|---|---|---|---|---|
| TNF 25 | 1.21 | 0/5 | 24.7 | 2.3 |
| +IMT 3.5 | 1.18 | 0/5 | 23.3 | 7.9 |
| +IMT 7.0 | 0.98 | 2/5 (d5) | 11.8 | 53.3 |
| TNF 50 | 1.23 | 0/5 | 19.3 | 23.7 |
| +IMT 3.5 | 1.11 | 0/5 | 5.9 | 76.7 |
| +IMT 7.0 | 1.05 | 0/5 | 3.8 | 85.0 |
| IMT 3.5 | 1.2 | 0/5 | 13.5 | 46.6 |
| 7.0 | 1.06 | 0/5 | 11.7 | 53.8 |
| CONTROL (PBS) | 1.16 | 0/5 | 25.3 | 0 |

In Table 3, substantially greater than additive results were obtained at both TNF levels (the corresponding IMT alone levels are found in Table 2).

TABLE 3

| group | ΔBW | deaths | ΔTW | % TGI |
|---|---|---|---|---|
| TNF 50 | 1.19 | 0/5 | 19.1 | 24.5 |
| +IMT 3.5 | 1.05 | 0/5 | 3.8 | 85.0 |
| +IMT 7.0 | 1.12 | 3/5 (d2,9,10) | 4.4 | 82.6 |
| TNF 100 | 1.23 | 1/5 (d6) | 22.5 | 11.1 |
| +IMT 3.5 | 1.28 | 4/5 (d5) | 2.5 | 90.1 |
| +IMT 7.0 | 0.99 | 1/5 (d5) | 5.2 | 79.5 |
| Control (cytoxan) | 1.11 | 0/5 | 2.4 | 90.5 |

(ΔTW for TNF 50 + IMT 7.0 and for TNF 100 + IMT 3.5 was determined on the basis of survivors)

A tabulated comparison of these simultaneous and alternating modes of administration is found in Table 4 which represents the average change in tumor weight at the 8 dosage level combinations used.

TABLE 4

|  | TNF 150 µg/kg | | 300 µg/kg | |
| --- | --- | --- | --- | --- |
|  | ΔTW (deaths) | ΔTW (deaths) | ΔTW (deaths) | ΔTW (deaths) |
| IMT dose | 3.5 | 7.0 | 3.5 | 7.0 |
| Simultaneous | 23.3 (0/5) | 11.8 (2/5) | 5.9 (0/5) | 3.8 (0/5) |
| Alternating | 3.8 (0/5) | 4.4 (3/5) | 2.5 (4/5) | 5.2 (1/5) |

The results are most striking at lower dose levels of TNF where it is clear that the alternative protocol produces superior results, showing a dramatic decline in the change in tumor weight as compared to simultaneous administration. However, the results also show that simultaneous administration is somewhat less toxic compared to alternating schedules.

I claim:

1. A composition which comprises a pharmacologically effective mixture of TNF and a suitable immunotoxin.

2. The composition of claim 1 which further includes a pharmaceutically acceptable excipient.

3. The composition of claim 1 wherein the immunotoxin comprises ricin A toxin.

4. The composition of claim 1 wherein the TNF is human TNF.

5. The composition of claim 4 wherein the human TNF is selected from mature human TNF, a mutein of mature human TNF lacking four amino acids at the N-terminus, and a mutein of mature human TNF lacking eight amino acids at the N-terminus.

6. The composition of claim 1 wherein the TNF is recombinantly produced.

7. The composition for therapeutic or prophylactic treatment of adenocarcinoma tumor burden in a warm-blooded animal subject which comprises a pharmacologically effective mixture of TNF and a suitable immunotoxin wherein said immunotoxin binds to said adenocarcinoma tumor.

8. A composition as described in claim 7, wherein said adenocarcinoma tumor burden is a human breast adenocarcinoma.

9. A method for treating adenocarcinoma tumor burden in a warm-blooded animal subject said method comprising administering to said animal subject a pharmaceutically effective amount of a combination of TNF with an immunotoxin said immunotoxin comprising an antibody 260F9 and a toxin, ricin A, wherein said immunotoxin (IMT) binds selectively to said adenocarcinoma tumor, and adiminsteration of said combination of TNF and immunotoxin is either as a single composition, or said TNF and immunotoxin are administered separately, or said TNF and immunotoxin are administered in a staggered or simultaneous dosage protocol.

* * * * *